United States Patent [19]

Mohiuddin et al.

[11] Patent Number: 5,070,877
[45] Date of Patent: Dec. 10, 1991

[54] NOVEL METHOD OF MYOCARDIAL IMAGING

[75] Inventors: Syed M. Mohiuddin; Daniel E. Hilleman, both of Omaha, Nebr.

[73] Assignee: MeDco Research, Inc., Los Angeles, Calif.

[21] Appl. No.: 330,156

[22] Filed: Mar. 29, 1989

Related U.S. Application Data

[63] Continuation-in-part of Ser. No. 231,217, Aug. 11, 1988, abandoned.

[51] Int. Cl.$^5$ .............................................. A61B 6/00
[52] U.S. Cl. ................................... 128/653.4; 600/4; 424/9; 514/46; 128/654
[58] Field of Search .................. 600/3, 4; 128/659 C; 424/9; 514/46, 47

[56] References Cited

U.S. PATENT DOCUMENTS

| | | | |
|---|---|---|---|
| 3,845,205 | 10/1974 | Maguire et al. | 514/46 |
| 4,663,313 | 5/1987 | Bristol et al. | 514/46 |
| 4,673,563 | 6/1987 | Berne et al. | 424/9 |
| 4,689,041 | 8/1987 | Cordy et al. | |
| 4,693,996 | 9/1987 | Steffen | 514/46 |
| 4,709,703 | 12/1987 | Lazarow et al. | 128/654 |
| 4,880,783 | 11/1989 | Mentzer et al. | 514/46 |

FOREIGN PATENT DOCUMENTS

| | | | |
|---|---|---|---|
| 0062921 | 10/1982 | European Pat. Off. | 514/46 |
| 2007273 | 8/1971 | Fed. Rep. of Germany | |
| WO83/02391 | 7/1983 | PCT Int'l Appl. | |
| WO87/01593 | 3/1987 | PCT Int'l Appl. | |

OTHER PUBLICATIONS

Camici et al., "A Multitrace Autoradigraphic Technique for Imaging Myocardial Flow and Metabolism", Conference: Computers in Cardiology, 1981: 159–162.
Hayden et al., "Scintiphotographic Studies of Acquired Cardiovascular Disease", Nuclear Medicine, vol. 3, No. 2, 1973, pp. 177–190.
Crystal et al., "Small Vessel and Total Coronary Blood Volume During Intracoronary Adenosine", AMJ Physiol. 241 (2), 1981, pp. 194–201.
Kwan et al., "Photoaffinity of Adnosine Transporter in Cardiac Membranes with Nitrobenzylthionosine", AM J Physiol 246 (5), 1984, 710–715.
Strauss et al., American Journal of Cardiology, vol. 39, pp. 403–406, (1977).
Rumberger et al., Journal of the American College of Cardiology, vol. 9, No. 1, pp. 59–69 (1987).
McCall et al., Canadian Journal of Cardiology, vol. 2, No. 3, pp. 176–183 (1986).
Biaggioni et al., Life Sciences, vol. 39, pp. 2229–2236 (1986).
Helmann et al., American Journal of Physiology, vol. 231, No. 5, pp. 1495–1500 (1976).
Watt et al., British Journal of Clinical Pharmacology, 24: pp. 665–668 (1987).
Wilson et al., Circulation, vol. 82, No. 5, pp. 1595–1606 (1990).
Zijlstra et al., Catheterization and Cardiovascular Diagnosis, 15: pp. 76–80 (1988).
Pantely et al., Circulation, vol. 82: pp. 1854–1856 (1990).

Primary Examiner—C. Fred Rosenbaum
Assistant Examiner—Mark O. Polutta
Attorney, Agent, or Firm—Pennie & Edmonds

[57] ABSTRACT

The parenteral use of adenosine, functional adenosine receptor agonists which include 1-methyl-2-phenylethyladenosine, 5-ethyl carboxamide adenosine, cyclopentyl adenosine and 2-chloro adenosine; metabolic precursors or by-products of adenosine which include adenine and inosine; and phosphorylated derivatives of adenosine including adenosine monophosphate, adenosine diphosphate and adenosine triphosphate in conjunction with various invasive and noninvasive diagnostic techniques to detect the presence or assess the severity of vascular disease is a novel application (indication) for these compounds and forms the basis of this patent application.

48 Claims, No Drawings

NOVEL METHOD OF MYOCARDIAL IMAGING

This application is a continuation-in-part of application Ser. No. 231,217 filed Aug. 11, 1988 now abandoned.

BACKGROUND OF THE INVENTION

Several invasive and noninvasive techniques are used to assess patients with known or suspected coronary artery disease. Included among the noninvasive methodologies are electrocardiography, radionuclide angiography (first pass and equilibrium studies utilizing, for example, technecium 99 m labeled red blood cells), myocardial perfusion scintigraphy (utilizing positron emitting radiopharmaceuticals, for example, thallium-201, rubidium-82, nitrogen-13), and echocardiography (M mode and two dimensional). The manifestations of coronary artery disease are a function of the balance between myocardial oxygen supply and demand. Although these noninvasive procedures may be performed in a resting subject, there may not be sufficient imbalance between supply and demand to detect abnormalities at rest. Therefore, provocative studies are frequently performed to improve the predictive accuracy of these diagnostic procedures. The most commonly employed provocative (stress) technique utilizes a standard exercise protocol. Under conditions of exercise myocardial oxygen demand is increased to exceed supply. This form of stress testing is commonly employed in conjunction with electrocardiography, radionuclide angiography, myocardial perfusion scintigraphy, echocardiography, and contrast ventriculography.

Recently, provocative studies have been developed utilizing pharmacological techniques designed to increase myocardial oxygen supply. Specifically, coronary vasodialators (e.g. nitrates, papavarine, dipyridamole, etc.) have been used for this purpose, although none have been approved by the FDA for this specific indication. While the mechanism is not clear, these agents may dilate normal vessels to a greater extent than diseased vessels, establishing a shunt or "myocardial steal". Pharmacological provocation may be particularly useful in patients who are unable to exercise, and may be equal to or superior to exercise provocation in patients capable of exercising. Furthermore, since exercise increases demand and coronary vasodilators increase supply, it is possible that the highest diagnostic yield will accrue when they are used in conjunction with one another.

Coronary arteriography is an invasive procedure which currently represents the "gold standard" for confirming the diagnosis of coronary artery disease. However, this procedure only establishes the anatomical severity of the disease and provides little information concerning the functional significance of visible lesions. Furthermore, small vessel disease may be present and beyond the resolution of currently available equipment. Recently, in an attempt to establish the functional significance of coronary lesions, coronary vasodilators have been administered by intracoronary injection or intravenous infusion and coronary blood flow is measured by one of several techniques, such as doppler flow catheters, videodensitometry, coronary sinus thermodilution, and radionuclide clearance of inert gases. These techniques are becoming more widely used to measure coronary flow reserve (i.e. reserve capacity) which provides important information concerning the functional significance of stenotic vessels. Although nitrates, papavarine, and dipyridamole have been used by some physicians for this purpose, no vasodilator has been approved by the FDA for this specific indication. The use of adenosine, 1-methyl-2-phenylethyl-adenosine, 5-ethyl carboxamide adenosine, cyclopentyl adenosine 2-chloro adenosine, adenine, inosine, adenosine monophosphate, adenosine diphosphate, or adenosine triphosphate, in conjunction with the above stated techniques to measure coronary flow reserve and assess the functional severity of stenotic vessels represents a novel application (indication) of our compound.

SUMMARY OF THE INVENTION

Briefly, the present invention comprises a method of detecting the presence or assessing the severity of vascular disease which includes the administration to the human host of an effective dilating amount of adenosine; functional adenosine receptor agonists (e.g., 1-methyl-2-phenylethyladenosine, 5-ethyl carboxamide adenosine, cyclopentyl adenosine or 2-chloro adenosine); metabolic precursors or byproducts of adenosine (e.g., adenine and inosine); and phosphorylated derivatives of adenosine (e.g., adenosine monophosphate, adenosine diphosphate, or adenosine triphosphate), in conjunction with invasive or noninvasive techniques.

It is an object of this invention to provide a new diagnostic method to aid in the determination of the extent and severity of heart disease.

It is a further object of this invention to provide a new radioimaging technique for the coronary arteries.

More particularly, it is one object of this invention to provide an improved method of radioimaging the coronary arteries.

It is one significant object of this invention to provide wash out times for the radiolabeled agents used in stress-free cardiac imaging which are comparable to the wash out times presently attainable only in stress or exercise radioimaging tests.

These and other objects and advantages will be apparent from the more detailed description which follows.

DETAILED DESCRIPTION OF THE INVENTION

Adenosine is chemically designated as 9-β-D-ribofuranosyl-9H-purine-6-amine; 6-amino-9-β-D-ribofuranosyl-9H-purine; 9-β-D-ribofuranosidoadenine; adenine riboside.

Adenosine is a nucleoside widely distributed in nature. factured from yeast nucleic acid. It is practically insoluble in alcohol. Crystals form from water, mp 234°-235°. $[\alpha]^{11} - 61.7°$ (c=0.706 in water; $[\alpha]^9 - 58.2°$ (c=658 in water). uv max: 260 nm (ε15,100).

The structural formula is as follows:

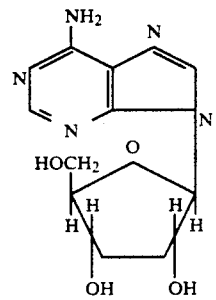

-continued

C₁₀H₁₃N₅O₄  267.24
Empirical Formula  Molecular Weight

This invention utilized adenosine administration as a pharmacological stressor in conjunction with any one of several noninvasive diagnostic procedures available. For example, intravenous adenosine may be used in conjunction with thallium-201 myocardial perfusion imaging to assess the severity of myocardial ischemia. In this case, anyone of several different radiopharmaceuticals may be substituted for thallium-201 (e.g. rubidium-82, technitium 99m, derivatives of technitium 99m, nitrogen-13, iodine 123, etc.). Similarly, adenosine may be administered as a pharmacological stressor in conjunction with radionuclide angiography to assess the severity of myocardial dysfunction. In this case, radionuclide angiographic studies may be first pass or gated equilibrium studies of the right and/or left ventricle. Similarly, adenosine may be administered as a pharmacological stressor in conjunction with echocardiography to assess the presence of regional wall motion abnormalities. Similarly, adenosine may be administered as a pharmacological stressor in conjunction with invasive measurements of coronary blood flow such as by intracardiac catheter to assess the functional significance of stenotic coronary vessels.

This invention typically involves the administration of adenosine by intravenous infusion in doses which are effective to provide coronary artery dilation (approximately 20-200 mcg/kg/min). However, its use in the invasive setting may involve the intracoronary administration of the drug in bolus doses of 2-20 mcg. The adenosine used in this invention is normally admixed with any pharmaceutically suitable carrier or carriers such as saline, dextrose, water, or any other carrier customarily used for the type of administration intended. The solution may contain the active ingredient in a widely varying amount, for example, from about 1 mg/ml to about 12 mg/ml.

These doses increase coronary flow approximately 4-5 times resting values. Unlike papavarine which in this setting frequently causes QT interval prolongation, significant electrocardiographic or systemic hemodynamic abnormalities have not been observed. Adenosine is a superior vasodilator for this purpose.

The practice of this invention is applicable to radiopharmaceuticals generally, and specifically to those mentioned hereinabove.

Contemplated as equivalents of adenosine in the practice of this invention are analogues, derivatives, metabolic precursors or by-products or conjugates intended to function as agonists of the adenosine receptor responsible for mediating vasodilation. This appears to be the A₂ receptor subtype. Several analogues of adenosine have been developed which appear to have greater affinity or specificity for the A₂ receptor. These include primarily the N₆ substituted derivatives and the 2-carbon derivatives such as 1-methyl-2-phenylethyl-adenosine, 5-ethyl carboxamide adenosine, cyclopentyl adenosine, 2-chloro adenosine, etc.

The following methods are preferred embodiments of our invention.

The method comprising the use of an agent which is adenosine, functional adenosine receptor agonists, metabolic precursors or by-products of adenosine, or phosphorylated derivatives of adenosine as a substitute for exercise in conjunction with myocardial perfusion imaging to detect the presence and/or assess the severity of coronary arter disease in humans wherein myocardial perfusion imaging is performed by any one of several techniques including radiopharmaceutical myocardial perfusion imaging, planar (conventional) scintigraphy, single photon emission computed tomography (SPECT), positron emission tomography (PET), nuclear magnetic resonance (NMR)imaging, perfusion contrast echocardiography, digital subtraction angiography (DSA), or ultrafast x-ray computed tomography (CINE CT).

The method comprising the use of an agent which is adenosine, functional adenosine receptor agonists, metabolic precursors or by-products of adenosine, or phosphorylated derivatives of adenosine as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide angiography.

The method comprising the use of an agent which is adenosine, functional adenosine receptor agonists, metabolic precursors or by-products of adenosine, or phosphorylated derivatives of adenosine as a coronary hyperemic agent in conjunction with means for measuring coronary blood flow velocity to assess the vasodilatory capacity (reserve capacity) of coronary arteries in humans wherein coronary blood flow velocity is measured by any one of several techniques including Doppler flow catheter, digital subtraction angiography or other radiopharmaceutical imaging technique.

The following Examples are to illustrate the invention, and are not intended to limit the invention.

EXAMPLE I

As set forth in this example, the effects of intravenous adenosine as a pharmacological stressor in conjunction with thallium 201 scintigraphy were evaluated. In the first set of experiments, adenosine was compared to exercise in a crossover study design using planar (conventional) thallium 201 scintigraphy in a population of 20 healthy normal volunteers. In the second set of studies, adenosine was compared to dipyridamole in a crossover study design using planar (conventional) thallium 201 scintigraphy in a population of 26 subjects (12 healthy volunteers and 14 patients with angiographically documented coronary artery disease). In the third set of experiments, adenosine was evaluated using thallium 201 single-photon emission computed tomography (SPECT) in a population of 33 patients (18 normal subjects and 15 patients with angiographically documented coronary artery disease).

In the first set of experiments, 20 healthy normal volunteers (age 19-39 years) underwent planar (conventional) stress/redistribution thallium 201 scintigraphy twice (in a random crossover design). One study employed maximum treadmill exercise (Bruce protocol) as the method of stress and the other study employed an intravenous infusion of adenosine as the method of stress. Heart rate, blood pressure and a 12-lead electrocardiogram were monitored throughout the study. The exercise stress test was conducted in standard fashion. The adenosine stress test employed a constant infusion of adenosine initiated at 20 mcg/kg/min. The infusion was doubled at intervals to a maximum dose of 140 mcg/kg/min. The maximum tolerable dose was administered for at least 5 minutes prior to a single bolus injection of thallium 201 (approximately 2.0 mCi). Early (stress) imaging was performed 5-10 minutes after the thallium injection and delayed (redistribution) imaging was performed 3-4 hours after thallium injection. The adenosine infusion was continued to the end of early imaging. Early and delayed imaging each consisted of 3 sets of images (left arterior oblique, anterior and left lateral projections). The images were acquired and reconstructed in standard fashion. The adenosine infusion was well tolerated in all subjects. The exercise stress images and the adenosine stress images were interpreted as normal (i.e., no perfusion defect detected) in all subjects. This experiment indicates that adenosine compares favorably to exercise in detecting normalcy by planar thallium 201 scintigraphy.

In the second set of experiments, 12 healthy normal volunteers and 14 patients with angiographically documented coronary artery disease underwent planar (conventional) stress/redistribution thallium 201 scintigraphy twice (in a random crossover design). One study employed oral dipyridamole (300 mg) as the method of stress and the other study employed an intravenous infusion of adenosine as the method of stress. Dipyridamole stress imaging was performed in standard fashion and adenosine stress imaging was performed as described above. Again, the adenosine infusion was well tolerated in all subjects. The sensitivity, specificity and overall predictive accuracy for detection of coronary artery disease was 88.8%, 87.5% and 88.0%, respectively, with adenosine imaging, and 77.7%, 82.6% and 80.5%, respectively, with dipyridamole imaging. The positive predictive value of adenosine and dipyridamole imaging was 84.2% and 77.7% respectively. This study indicates that adenosine imaging is safe and may be superior to dipyridamole imaging for the accurate detection of angiographically significant coronary artery disease.

In the third set of experiments, 15 patients with angiographically documented coronary artery disease and 18 subjects with either angiographically normal coronary arteries (n=8) or healthy normal volunteers (n=10) underwent thallium 201 myocardial perfusion imaging using single photon emission computed tomography (SPECT). In all subjects, only an infusion of adenosine was employed as a method of stress. The adenosine infusion was initiated at 50 mcg/kg/min and titrated at 1 minute intervals by increments of 25 mcg/kg/min to a maximum dose of 140 mcg/kg/min. The maximum tolerable dose was maintained for at least 1 minute prior to and 3 minutes subsequent to a single bolus injection of thallium 201 (approximately 3.0 mCi). Early (stress) imaging was performed 5-10 minutes post-thallium and delayed (redistribution) imaging was performed 3-4 hours post-thallium. The SPECT images were acquired and reconstructed in standard fashion. Side effects occurred in 76% of the subjects, but were usually mild, did not require therapy and ceased instantly after discontinuing the adenosiene infusion. Chest pain occurred in 53%, headache in 34% and cutaneous flushing in 15%. Dose-dependent decreases is systolic blood pressure (hypotension) and reflex increases in heart rate were common. Perfusion defects were detected during adenosine stress imaging in all 15 patients with known coronary artery disease and these defects were reversible in 9 (sensitivity =100%). The adenosine stress images were interpreted as normal in 16 of 18 presumed healthy subjects (specificity =89%). This study indicates that adenosine-induced coronary vasodilation is a safe, convenient, and potent intervention to uncover perfusion defects during SPECT thallium scintigraphy in patients with coronary artery disease.

EXAMPLE II

As set forth in this example, the effects of intravenous adenosine as a pharmacological stressor in conjunction with echocardiography were evaluated.

Fifteen patients with a positive exercise (stress) SPECT thallium 201 tomogram were selected for this study. The tomographic perfusion defect was fixed (irreversible) in 6 subjects and reversible in 9 subjects. Subsequently, these patients underwent standard 2-dimensional echocardiographic studies under conditions of rest (baseline) and during an intravenous infusion of adenosine as previously described (Example I, 3rd set of experiments). Echocardiographic studies were performed over a 1 minute period prior to the adenosine infusion (baseline), during maximum adenosine infusion (140 mcg/kg/min), and 3 minutes after the cessation of the adenosine infusion. All echocardiographic studies included parasternal views (long axis and short axis at the level of the mitral valve, papillary muscles and apex) and apical views (4-chamber, 2-chamber and apical long axis). All echocardiogrpahic images were interpreted by standard qualitative and quantitative techniques. The echocardiographic images obtained at rest were interpreted as normal in all subjects. However, left ventricular wall motion abnormalities were detected during adenosine (stress) studies in all 6 patients with fixed thallium perfusion defects. Left ventricular wall motion remained normal during the adenosine infusion in all patients with reversible thallium perfusion defects. This study indicates that adenosine may be a useful pharmacological stressor for the detection if ischemic ventricular dysfunction as assessed by echocardiography.

EXAMPLE III

As set forth in this example, the effects of intravenous and intracoronary adenosine as a pharmacological stressor in conjunction with measurements of coronary blood flow reserve (CBFR) were evaluated at the time of coronary arteriography using a Doppler flow catheter.

Ten patients with an angiographically normal left coronary artery were studied at the time of diagnostic coronary arteriography. A 3F Doppler catheter was positioned in the left coronary artery to measure coronary blood flow velocity (CBFV), and mean arterial pressure, heart rate and the ECG were simultaneously recorded. Following repeated measures of baseline CBFV, incremental doses of intracoronary papaverine (8-12 mg boluses), intracoronary adenosine (4-14 mcg boluses) and intravenous adenosine (70-140 mcg/kg/min infusions) were administered in crossover fashion. Each drug was titrated to the maximum coronary hyperemic response. While the ECG intervals were unchanged during adenosine administration, papaverine routinely prolonged the QT interval (mean 96±18 msec). Relative to papaverine, maximum coronary hyperemic responses (4-5 fold increases in CBFV) were achieved with 14 mcg intracoronary bolus doses of adenosine, as well as 140 mcg/kg/min intravenous infusions of adenosine. Compared to papaverine, maximal coronary hyperemia occurred sooner with adenosine (10 vs 20 seconds) and resolved sooner with adenosine (37 vs 118 seconds), consistent with its ultrashort half-life. This study indicates that maximal coronary hyperemia can be achieved with either intracoronary or intravenous adenosine and may be a useful technique to assess the vasodilatory reserve capacity (i.e., functional significance) of stenotic coronary vessels.

ADVANTAGES OF THIS INVENTION OVER CONVENTIONAL TECHNIQUES

Certainly, adenosine and the other analogs mentioned hereinabove as a pharmacological stressor have the advantage over exercise as a stressor in patients who are unable or are unwilling to exercise at a work load appropriate for the noninvasive assessment of coronary artery disease. It remains to be determined whether these compounds as a pharmacological stressor are superior to exercise as a stressor in the assessment of coronary artery disease among patients capable of exercising. Although no coronary vasodilators have been approved by the Food and Drug Administration for this indication, adenosine and the related compounds identified above possess several advantages over the other conventional agents such as, nitrates, papavarine, and dipyridamole. First, adenosine has an ultra short half-life (less than 20 seconds). As a result, its onset of action and clearance from the body are rapid and the time required to perform the procedure is shortened. Furthermore, side effects when they occur are rapidly controlled by reducing the infusion rate and rarely require discontinuing the infusion or treating with theophylline. Second, adenosine is an endogenous substance in humans and should not result in allergic reactions.

Having fully described the invention it is intended that it be limited solely by the lawful scope of the appended claims.

We claim:

1. A method of detecting the presence and assessing the severity of myocardial dysfunction in a human comprising the steps of:
   (a) administering by an intravenous route to said human about 20 mcg/kg/minute to about 200 mcg/kg/minute of an adenosine receptor agonist sufficient to provide coronary artery dilation; and
   (b) performing a technique on said human to detect the presence and assess the severity of said myocardial dysfunction.

2. A method of detecting the presence and assessing the severity of myocardial dysfunction in a human comprising the steps of:
   (a) administering by an intracoronary route to said human about 2 mcg to about 20 mcg of an adenosine receptor agonist sufficient to provide coronary artery dilation; and
   (b) performing a technique on said human to detect the presence and assess the severity of said myocardial dysfunction.

3. The method of claim 1 or 2, wherein said myocardial dysfunction is selected from the group consisting of coronary artery disease, ventricular dysfunction and differences in blood flow through disease free coronary vessels and stenotic coronary vessels.

4. The method of claim 1 or 2, wherein said adenosine receptor agonist is selected from the group consisting of adenosine, 1-methyl-2-phenylethyl-adenosine, 5-ethyl carboxamide-adenosine, cyclopentyl adenosine, 2-chloro adenosine, adenine, inosine, adenosine monophosphate, adenosine diphosphate and adenosine triphosphate.

5. The method of claim 1 or 2, wherein said technique to detect the presence and assess the severity of myocardial dysfunction is selected from the group consisting of radiopharmaceutical myocardial perfusion imaging when said myocardial dysfunction is coronary artery disease, ventricular function imaging when said myocardial dysfunction is ventricular dysfunction and a method for measuring coronary blood flow velocity when said myocardial dysfunction is the difference in blood flow through disease free coronary vessels as opposed to stenotic coronary vessels.

6. The method of claim 1 wherein said adenosine receptor agonist is administered by intravenous infusion in a dosage of about 140 mcg/kg/minute.

7. The method of claims 1, 2 or 6, wherein said adenosine receptor agonist is adenosine.

8. The method of claim 3 wherein said adenosine receptor agonist is adenosine.

9. The method of claim 4 wherein said adenosine receptor agonist is adenosine.

10. The method of claim 1 wherein said radiopharmaceutical myocardial perfusion imaging is selected from the group consisting of scintigraphy, single photon emission computed tomography (SPECT), positron emission tomography (PET), nuclear magnetic resonance (NMR) imaging, perfusion contrast echocardiography, digital subtraction angiography (DSA) and ultrafast X-ray computed tomography (CINE CT).

11. The method of claim 10 wherein the radiopharmaceutical agent used in conjunction with said radiopharmaceutical myocardial perfusion imaging is selected from the group consisting of thallium-201, technetium-99m, derivatives of technetium-99m, nitrogen-13, rubidium-82 iodine-123 and oxygen-15.

12. The method of claim 11 wherein said radiopharmaceutical myocardial perfusion imaging technique is scintigraphy and said radiopharmaceutical agent is thallium-201.

13. The method of claim 5 wherein said ventricular function imaging technique is selected from the group consisting of echocardiography, contrast ventriculography and radionuclide angiography.

14. The method of claim 13 wherein said ventricular function imaging technique is echocardiography.

15. The method of claim 5 wherein said method for measuring coronary blood flow velocity is selected from the group consisting of doppler flow catheter, digital subtraction angiography and radiopharmaceutical imaging techniques.

16. The method of claim 15 wherein said method for measuring coronary blood flow velocity is doppler flow catheter.

17. A method of detecting the presence and assessing the severity of coronary artery disease in a human comprising the steps of:
   (a) administering by an intravenous route to said human about 20 mcg/kg/minute to about 200 mcg/kg/minute of an adenosine receptor agonist sufficient to provide coronary artery dilation
   (b) administering a radiopharmaceutical agent into said human; and
   (c) performing radiopharmaceutical myocardial perfusion imaging on said human in order to detect the presence and assess the severity of coronary artery disease.

18. The method of claim 17 wherein said adenosine receptor agonist is administered by intravenous infusion in a dosage of about 140 mcg/kg/minute.

19. A method of detecting the presence and assessing the severity of coronary artery disease in a human comprising the steps of:
   (a) administering by an intracoronary route to said human about 2 mcg to about 20 mcg of an adenosine receptor agonist sufficient to provide coronary artery dilation;
   (b) administering a radiopharmaceutical agent into said human; and
   (c) performing radiopharmaceutical myocardial perfusion imaging on said human in order to detect the presence and assess the severity of coronary artery disease.

20. The method of claim 17 or 19, wherein said adenosine receptor agonist is selected from the group consisting of adenosine, 1-methyl-2-phenylethyl-adenosine, 5-ethyl carboxamide-adenosine, cyclopentyl adenosine, 2-chloro adenosine, adenosine, inosine, adenosine monophosphate, adenosine diphosphate and adenosine triphosphate.

21. The method of claim 17 or 19, wherein said radiopharmaceutical agent is selected from the group consisting of thallium-201, technetium-99m, derivatives of technetium-99m, nitrogen-13, rubidium-82 iodine-123 and oxygen-15.

22. The method of claim 17 or 19, wherein said radiopharmaceutical myocardial perfusion imaging is selected from the group consisting of scintigraphy, single photon emission computed tomography (SPECT), positron emission tomography (PET), nuclear magnetic resonance (NMR) imaging, perfusion contrast echocardiography, digital subtraction angiography (DSA) and ultrafast X-ray computed tomography (CINE CT).

23. The method of claim 17, 19 or 18, wherein said adenosine receptor agonist is adenosine.

24. The method of claim 20 wherein said adenosine receptor agonist is adenosine.

25. The method of claim 21 wherein said radiopharmaceutical agent is thallium-201.

26. The method of claim 22 wherein said radiopharmaceutical myocardial perfusion imaging is scintigraphy.

27. A method of detecting the presence and assessing the severity of ventricular dysfunction caused by coronary artery disease, in a human, comprising the steps of:
   (a) administering by an intravenous route to said human about 20 mcg/kg/minute to about 200 mcg/kg/minute of an adenosine receptor agonist sufficient to provide coronary artery dilation;
   (b) performing a ventricular function imaging technique on said human; and
   (c) determining the presence and assessing the severity of ventricular dysfunction.

28. A method of detecting the presence and assessing the severity of ventricular dysfunction caused by coronary artery disease, in a human, comprising the steps of:
   (a) administering by an intravenous route to said human about 2 mcg to about 20 mcg of an adenosine receptor agonist sufficient to provide coronary artery dilation;
   (b) performing a ventricular function imaging technique on said human; and
   (c) determining the presence and assessing the severity of ventricular dysfunction.

29. The method of claim 27 or 28, wherein said adenosine receptor agonist is selected from the group consisting of adenosine, 1-methyl-2-phenylethyl-adenosine, 5-ethyl carboxamide-adenosine, cyclopentyl adenosine, 2-chloro adenosine, adenine, inosine, adenosine monophosphate, adenosine diphosphate and adenosine triphosphate.

30. The method of claim 27 or 28, wherein said ventricular function imaging technique is selected from the group consisting of echocardiography, contrast ventriculography and radionuclide angiography.

31. The method of claim 27 wherein said adenosine receptor agonist is administered by intravenous infusion in a dosage of about 140 mcg/kg/minute.

32. The method of claim 27, 28 or 31, wherein said adenosine receptor agonist is adenosine.

33. The method of claim 29 wherein said adenosine receptor agonist is adenosine.

34. The method of claim 30 wherein said ventricular function imaging technique is echocardiography.

35. A method of determining the difference between the coronary blood flow through disease free coronary vessels and stenotic coronary vessels in a human comprising the steps of:
   (a) administering by an intravenous route to said human about 20 mcg/kg/minute to about 200 mcg/kg/minute of an adenosine receptor agonist sufficient to provide coronary artery dilation;
   (b) performing a method for measuring coronary blood flow velocity on said human in order to assess the vasodilatory capacity of disease free coronary vessels as opposed to stenotic coronary vessels.

36. The method of claim 35 wherein said adenosine receptor agonist is administered by intravenous infusion in a dosage of about 140 mcg/kg/minute.

37. A method of determining the difference between the coronary blood flow through disease free coronary vessels and stenotic coronary vessels in a human comprising the steps of:
   (a) administering by an intracoronary route to said human about 2 mcg to about 20 mcg of an adenosine receptor agonist sufficient to provide coronary artery dilation;
   (b) performing a method for measuring coronary blood flow velocity on said human in order to assess the vasodilatory capacity (reserve capacity) of disease free coronary vessels as opposed to stenotic coronary vessels.

38. The method according to claim 35 or 37, wherein said adenosine receptor agonist is selected from the group consisting of adenosine, 1-methyl-2-phenylethyl-adenosine, 5-ethyl carboxamide-adenosine, cyclopentyl adenosine, 2-chloro adenosine, adenine, inosine, adenosine monophosphate, adenosine diphosphate and adenosine triphosphate.

39. The method of claim 35 or 37, wherein said method for measuring coronary blood flow velocity is selected from the group of Doppler flow catheter, digital subtraction angiography and radiopharmaceutical imaging techniques.

40. The method of claim 35, 37 or 36, wherein said adenosine receptor agonist is adenosine.

41. The method of claim 38 wherein said adenosine receptor agonist is adenosine.

42. The method of claim 39 wherein said method for measuring coronary blood flow velocity is doppler flow catheter.

43. A method of detecting the presence and assessing the severity of coronary artery disease in a human comprising the steps of:

(a) administering to said human by intravenous infusion about 20 mcg/kg/minute to about 200 mcg/kg/minute of adenosine in order to provide coronary artery dilation;
(b) administering thallium-201 to said human; and
(c) performing the scintigraphy on said human in order to detect the presence and assess the severity of coronary artery disease.

44. A method of detecting the presence and assessing the severity of ventricular dysfunction in a human comprising the steps of:
(a) administering to said human by intravenous infusion about 20 mcg/kg/minute to about 200 mcg/kg/minute of adenosine in order to provide coronary artery dilation;
(b) performing an echocardiography on said human; and
(c) determining the presence and assessing the severity of ventricular dysfunction.

45. A method of determining the difference between coronary blood flow through disease free coronary vessels and stenotic coronary vessels in a human comprising the steps of:
(a) administering to said human by intracoronary bolus injection about 2 mcg to about 20 mcg of adenosine, in order to provide coronary artery dilation;
(b) measuring the difference between coronary blood flow through disease-free coronary vessels and stenotic coronary vessels in said human using a doppler flow catheter in order to assess the vasodilatory capacity (reserve capacity) of disease-free coronary vessels as opposed to stenotic coronary vessels.

46. A method of detecting the presence and assessing the severity of coronary artery disease in a human comprising the steps of:
(a) administering to said human by intracoronary bolus injection about 2 mcg to about 20 mcg of adenosine in order to provide coronary artery dilation;
(b) administering thallium-201 to said human; and
(c) performing scintigraphy on said human in order to detect the presence and assess the severity of coronary artery disease.

47. A method of detecting the presence and assessing the severity of ventricular dysfunction in a human comprising the steps of:
(a) administering to said human by intracoronary bolus injection about 2 mcg to about 20 mcg of adenosine in order to provide coronary artery dilation;
(b) performing an echocardiography on said human; and
(c) determining the presence and assessing the severity of ventricular dysfunction.

48. A method of determining the difference between coronary blood flow through disease free coronary vessels and stenotic coronary vessels in a human comprising the steps of:
(a) administering to said human by intravenous infusion about 20 mcg/kg/minute to about 200 mcg/kg/minute of adenosine, in order to provide coronary arter dilation;
(b) measuring the difference between coronary blood flow through disease-free coronary vessels and stenotic coronary vessels in said human using a Doppler flow catheter in order to assess the vasodilatory capacity (reserve capacity) of disease-free coronary vessels as opposed to stenotic coronary vessels.

* * * * *

UNITED STATES PATENT AND TRADEMARK OFFICE

CERTIFICATE EXTENDING PATENT TERM
UNDER 35 U.S.C. § 156

PATENT NO.      :   5,070,877

ISSUED          :   December 10, 1991

INVENTOR(S)     :   Syed M. Mohiuddin et al.

PATENT OWNER    :   Medco Research Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 159 days from the original expiration date of the patent, December 10, 2008, with all rights pertaining thereto as provided by 35 U.S.C. § 156(b).

I have caused the seal of the Patent and Trademark Office to be affixed this 6th day of January 1997.

Bruce A. Lehman
Assistant Secretary of Commerce and
  Commissioner of Patents and Trademarks